United States Patent [19]

Nishikawa et al.

[11] Patent Number: 5,728,852
[45] Date of Patent: Mar. 17, 1998

[54] METHOD FOR PRODUCING MONOHYDROXYALKYLAMIDES

[75] Inventors: Kenichi Nishikawa; Kazuhito Miyoshi; Yukiko Oshima; Hiroyuki Imoto, all of Wakayama, Japan

[73] Assignee: KAO Corporation, Tokyo, Japan

[21] Appl. No.: 694,022

[22] Filed: Aug. 8, 1996

[30] Foreign Application Priority Data

Aug. 9, 1995 [JP] Japan ................... 7-225911
Dec. 28, 1995 [JP] Japan ................... 7-354491

[51] Int. Cl.$^6$ ................................... C07C 231/02
[52] U.S. Cl. ................... 554/66; 554/61; 554/69; 564/141
[58] Field of Search ................... 554/66, 69, 61; 564/141

[56] References Cited

U.S. PATENT DOCUMENTS

| | | | |
|---|---|---|---|
| 2,843,612 | 7/1958 | Ricciardi et al. | 551/66 |
| 2,844,609 | 7/1958 | Tesoro | 554/66 |
| 3,024,260 | 3/1962 | Ernst | 554/66 |
| 3,387,008 | 6/1968 | Cawley | 554/66 |

FOREIGN PATENT DOCUMENTS

| | | | |
|---|---|---|---|
| 2129425 | 12/1972 | Germany | 554/66 |
| 36-13622 | 8/1961 | Japan . | |
| 168681 | 2/1965 | U.S.S.R. | 554/66 |

OTHER PUBLICATIONS

Database WPI, Derwent Publications, AN-78-39468A, JP 56-49903, Nov. 25, 1981.

*Primary Examiner*—Shailendra Kumar
*Attorney, Agent, or Firm*—Oblon, Spivak, McClelland, Maier & Neustadt, P.C.

[57] ABSTRACT

A method for producing a monoalkanol amide comprising the steps of (a) treating an entire amount of fatty acid with a monoalkanol amine in an amount of 0.7 to 0.95 times by mole of the amount of the fatty acid and more than 70% and not more than 90% by weight of the entire amount of the monoalkanol amine to yield a mixture mainly containing a monoalkanol amide and an amido monoester; and (b) treating the mixture obtained in step (a) with the remaining portion of the monoalkanol amine, wherein the molar ratio of the entire amount of the monoalkanol amine to that of the fatty acid is 1.0 to 1.3.

19 Claims, 1 Drawing Sheet

METHOD FOR PRODUCING MONOHYDROXYALKYLAMIDES

BACKGROUND OF THE INVENTION

1. Field of the Invention

The present invention relates to a method for producing a highly pure monohydroxyalkylamide (hereinafter referred to as monoalkanol amide) by which the amount of residual fatty acid and the formation of by-products are significantly reduced.

2. Discussion of the Related Arts

Monoalkanol amides and various derivatives thereof including alkylene oxide adducts, and further modified derivatives, such as carboxymethylated derivatives, phosphorylated derivatives, and sulfuric acid ester derivatives, have found extensive applications as dispersants, emulsion stabilizers, or dye dispersants used in shampoo, liquid detergent, cream, etc. In order to produce alkanol amides, the following various methods have been described: (1) Alkanol amides are produced by the reaction between fatty acid esters and alkanol amines in the presence of an alkali catalyst (U.S. Pat. No. 2,844,609); (2) Alkanol amides are produced by treating fatty acid esters with alkanol amines at a molar ratio of 1:2 (fatty acid esters: alkanol amines) (JP-B-36-13622); (3) Alkanol amides are produced by treating fatty acids with alkanol amines to yield amido esters, and adding to the reaction mixture alkanol amines in which an alkali catalyst is uniformly dissolved or dispersed (JP-B-56-49903); and (4) In a first step, fatty acids are treated with diethanolamine in an amount not less than 1.01 times the amount of fatty acids to yield diethanolamide and bi-products which are amino ester and amido ester; and in a second step, an alkali catalyst is added to the reaction mixture to make the amino ester and amido ester formed in the first step react with unreacted diethanolamine (U.S. Pat. No. 3,024,260).

However, the above conventional methods are not free from drawbacks. Method (1) is economically disadvantageous because relatively expensive fatty acid esters are used as the starting materials. In method (2), fatty acid esters or fatty acids are treated with excess alkanol amines and a large amount of the alkanol amines remain in the final product, resulting in alkanol-amides of low purity.

Though method (3) is suitable for producing diethanolamide by treating a fatty acid with diethanolamine, it is not suitable for producing a monoalkanol amide by treating a fatty acid with a monoalkanol amine. If the reaction conditions in this method are applied to the production of a monoalkanol amide, that is, if the fatty acid is treated, in the first step, with a monoalkanol amine in an amount not less than 1.05 times the equivalent amount of the fatty acid in terms of the number of active hydrogen atoms in the amino and hydroxyl groups of the monoalkanol amine and less than 70% of the entire amount of the monoalkanol amine, a large amount of unreacted fatty acid remains because the selectivity of the reaction toward the formation of monoalkanol amide is low (see Comparative Example 2 of the present specification). As a result, the amount of alkali catalyst required for the reaction should undesirably be increased according to the amount of the unreacted fatty acid remaining.

In method (4), a large amount of amino ester is formed as a by-product and the reaction of the amino ester with unreacted diethanolamine takes a long time. Therefore it is time-consuming to obtain highly pure diethanolamide by this method. This drawback discourage applying this method to the production of monoalkanol amides.

In general, the above conventional methods employ high reaction temperatures, which causes the problem of significant discoloration of the reaction products. This problem has not been resolved with derivatives, making it difficult to yield a final product with a good hue.

SUMMARY OF THE INVENTION

Accordingly, an object of the present invention is to provide a method for producing a highly pure monoalkanol amide with significantly reduced amounts of residual fatty acid and by-products.

Another object of the present invention is to produce a monoalkanol amide without any undesirable discoloration.

In an effort to achieve the above objects, the present inventors have made intensive studies on the production of monoalkanol amides (monohydroxyalkylamides) by the reaction between fatty acids and monoalkanol amines (monohydroxyalkylamines).

The inventors studied selectivity of the reaction, i.e., selectivity toward monoalkanol amide formation, amido ester formation and amino ester formation. As a result, it has now been surprisingly found that the reaction selectivity toward monoalkanol amide formation increases when the amount of monoalkanol amine is in excess of the fatty acid, and that the selectivity toward amido ester formation increases when the amount of fatty acid is in excess of the monoalkanol amine. The inventors have also found that the selectivity toward amino ester formation is maximized when the molar ratio of monoalkanol amides to fatty acids is around 1 (FIG. 1).

Further, it has now been surprisingly found that monoalkanol amides with significantly reduced amounts of residual fatty acids and by-products can be obtained by the steps of (a) treating, as a first step reaction, an entire amount of fatty acid with a portion of monoalkanol amine under the conditions which permit no amino ester formation and which significantly reduce the amount of unreacted fatty acid to yield a mixture mainly containing monoalkanol amide and amido monoester with significantly reduced amount of residual or unreacted fatty acid, wherein the remaining portion of monoalkanol amine is a minimum necessary amount for a second step reaction; and (b) treating, as a second step reaction, the mixture obtained in step (a) with the remaining portion of monoalkanol amine in the presence of an alkali catalyst to transform the amido monoester to the monoalkanol amide, the molar ratio of the entire amount of monoalkanol amine to the entire amount of fatty acid being around 1.0 to 1.3.

The present inventors have surprisingly found that a monoalkanol amide with an extremely good hue can be produced by carrying out the second step reaction in the presence of an inorganic reducing agent.

Incidentally, since the residual or unreacted amount of fatty acids in the reaction mixture is very small at the completion of the first step, the amount of alkali catalyst used in the second step can be advantageously reduced. This is an advantage of the present invention over the method disclosed in JP-B-56-49903 because the amounts of residual fatty acids and alkali catalyst used in the second step can be reduced.

In one embodiment, the present invention relates to a method for producing a monoalkanol amide comprising the steps of:

(a) treating, as a first step, an entire amount of a fatty acid with a portion of a monoalkanol amine in an amount of 0.70 to 0.95 times the amount of the fatty acid by mole wherein the portion of the monoalkanol amine is more than 70% and not more than 90% by weight of the entire amount of the monoalkanol amine to yield a mixture mainly containing a monoalkanol amide and an amido monoester; and (b) treating, as a second step, the mixture obtained in step (a) with the remaining portion of the monoalkanol amine, wherein the molar ratio of the entire amount of the monoalkanol amine to that of the fatty acid is 1.0 to 1.3.

DETAILED DESCRIPTION OF THE INVENTION

Figure 1:
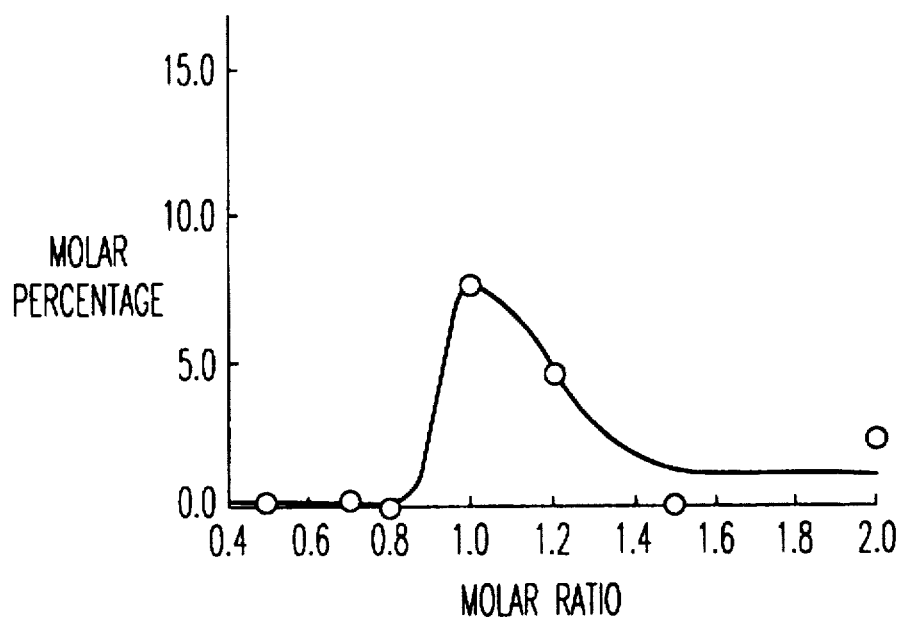
FIG. 1 is a graph which shows the effect of the molar ratio of monoalkanol amine to fatty acid on the reaction selectivity toward amino ester formation.

The monoalkanol amide produced by the method of the present invention is represented by the following general formula (4):

$$R-\underset{\underset{O}{\|}}{C}-NH-R'-OH \quad (4)$$

wherein R represents an alkyl or alkenyl group having 7 to 21 carbon atoms; R' represents an alkylene group having 1 to 5 carbon atoms.

The compounds represented by the above general formula include monoethanolamide, monomethanolamide, monopropanolamide, monoisopropanolamide, and monobutanolamide, with a preference given to monoethanolamide.

In the present invention, monoalkanol amides as mentioned above are produced from fatty acids and monoalkanol amines.

The fatty acids in the present invention are not particularly limited, and higher fatty acids as represented by the following general formula (2) are preferably used:

$$R^1COOH \quad (2)$$

wherein $R^1$ represents a linear or branched alkyl, alkenyl or hydroxyalkyl group having 7 to 23 carbon atoms. $R^1$ is preferably a linear or branched alkyl group having 7 to 19 carbon atoms, and more preferably a linear alkyl group having 9 to 13 carbon atoms.

Specific examples of the fatty acids include capric acid, caprylic acid, undecanoic acid, lauric acid, myristic acid, pentadecanoic acid, palmitic acid, stearic acid, oleic acid, arachidic acid, behenic acids, and fatty acids derived from coconut oil, beef tallow, palm oil, and palm kernel oil, and synthetic fatty acids obtained by paraffin oxidation or by the oxo process.

The monoalkanol amines in the present invention are not particularly limited, and the compounds represented by the following general formula (3) are preferably used:

$$R^2-NH_2 \quad (3)$$

wherein $R^2$ represents a linear alkanol group having 1 to 4 carbon atoms or a branched alkanol group having 3 or 4 carbon atoms. Specific examples include monomethanolamine, monoethanolamine, and monoisopropanolamine, with a preference given to monoethanolamine.

The method of the present invention is carried out in two steps. Specifically, an entire amount of a monoalkanol amine is divided into two portions to be used in each step, and different conditions are employed in each step. As for the fatty acid, the entire amount is used in the first step reaction.

First step

In the first step, an entire amount of a fatty acid is treated with a monoalkanol amine in an amount 0.70 to 0.95 times by mole of the amount of the fatty acid and more than 70% and not more than 90% by weight of the entire amount of the monoalkanol amine. In this reaction, a mixture mainly containing a monoalkanol amide and an amido monoester is produced. The amount of monoalkanol amine used in the first step reaction is preferably 75 to 85% and more preferably 75 to 80% by weight of the entire amount of the monoalkanol amine. The amount of monoalkanol amine used in the first step reaction is preferably more than 70%, more preferably more than 75%, by weight of the entire amount in view of supplying a sufficient amount of monoalkanol amine for the reaction with fatty acid, and not more than 90%, preferably not more than 85%, more preferably not more than 80% by weight of the entire amount in order to set aside a necessary amount of monoalkanol amine for the second step reaction. In order to decrease amino ester formation and residual fatty acids, the amount of monoalkanol amine added in the first step reaction is 0.70 to 0.95 times by mole of the amount of fatty acid, preferably 0.70 to 0.90 times by mole, and more preferably 0.75 to 0.85 times by mole.

Incidentally, the technical idea of the invention disclosed in JP-B-56-49903 is that a reduced amount of alkanol amine is used to form an amido ester as the main product of the first step reaction, followed by aminolysis of the amido ester to obtain an alkanol amide in the second step. On the other hand, in the present invention, as large of an amount as possible of monoalkanol amine is used to produce a large amount of monoalkanol amide and reduce the amount of residual fatty acid in the first step, thereby reducing the amount of alkali catalyst used in the second step.

Though there is no particular limitation to the reaction temperature, the reaction is carried out preferably at a temperature of from 100° to 170° C., more preferably from 130° to 165° C., most preferably from 140° to 160° C. In a preferred embodiment, the fatty acid is heated in advance to a temperature in the above range. The reaction temperature is preferably not less than 100° C. in view of maintaining an acceptable reaction speed, and not higher than 170° C. in view of suppressing leakage and coloration of monoalkanol amine.

The entire amount of monoalkanol amine used in the first and second steps is determined such that the molar ratio of the entire amount of monoalkanol amine to the entire amount of fatty acid is 1.0 to 1.3, preferably 1.0 to 1.1, and more preferably 1.00 to 1.05. The molar ratio is preferably not less than 1.0 in order to reduce the amount of amido ester formed in the reaction and the amount of residual fatty acid, and not more than 1.3 in order to prevent the lowering of purity and coloration of monoalkanol amide.

The pressure applied during the first step is not particularly limited, but it is preferred to reduce the pressure in order to promote amidoesterification, a dehydration reaction. The pressure is reduced to 3 mm Hg— atmospheric pressure, preferably to 3–50 mm Hg, 2 to 7 hours, preferably 2.5 to 5 hours after the start of the reaction. The pressure applied during the reaction is preferably not less than 3 mm Hg in order to prevent the reaction mixture from flowing out of the reaction system. When the reaction is carried out under atmospheric pressure, it is carried out preferably under purging with an inert gas, preferably nitrogen gas because dehydration is facilitated.

The duration of the reaction is not particularly limited, and the reaction is continued preferably for 7 to 13 hours.

Second step

The second step of the present invention has the following two embodiments: (Embodiment 1) The reaction is carried out by adding the remaining portion of monoalkanol amine to the mixture obtained in the first step reaction, wherein an alkali catalyst may be used. (Embodiment 2) The reaction is carried out by adding the remaining portion of monoalkanol amine to the mixture obtained in the first step reaction in the presence of an alkali catalyst and an inorganic reducing agent.

Embodiment 1

In the second step, the remaining portion of monoalkanol amine is added to the reaction mixture of the first step. The reaction temperature is not particularly limited, and it is determined according to the melting point of monoalkanol amide. For example, when the melting point of monoalkanol amide is not higher than 80° C., the reaction temperature is preferably 85° to 110° C., more preferably 90° to 100° C. The reaction temperature is preferably not less than 85° C. in order to maintain the reaction speed at an acceptable level, and not more than 110° in order to prevent deterioration of hue or color. The duration of reaction is not particularly limited, but it is preferred to continue the reaction for 0.1 to 2.0 hours.

The second step is carried out preferably in the presence of an alkali catalyst because the transformation of amido ester to monoalkanol amine is facilitated. As the alkali catalyst, metal alkoxides are preferably used, and preferred examples of metal alkoxides include sodium methylate, sodium ethylate, potassium methylate, and potassium methylate. The amount of an alkali catalyst is not particularly limited, but when considering the moisture in the reaction system, it is preferred to add the alkali catalyst in an amount of at least 0.3 to 10.0 mole % of the amount of the starting fatty acid. For the stability of the reaction, the amount of the catalyst is preferably 1.0 to 6.0 mole %. When the moisture of the reaction system can be reduced, the amount of the alkali catalyst is further reduced preferably to 0.3 to 2.0 mole % of the amount of the starting fatty acid.

The time when the alkali catalyst is added to the reaction system is not particularly limited, and it may be added at any time during the second step reaction.

Embodiment 2

In the second step, the remaining portion of monoalkanol amine is added to the reaction mixture obtained after the first step in the presence of an alkali catalyst and an inorganic reducing agent.

The alkali catalyst is not particularly limited, and the same catalysts as mentioned in Embodiment 1 may be used. The timing and amount of adding the catalyst are the same as those in Embodiment 1.

The inorganic reducing agents usable in the present invention include hydrogen, sodium sulfite, potassium sulfite, sodium thiosulfate, potassium thiosulfate, borohydride salts, and aluminum hydride salts, with a preference being given to borohydride salts represented by the following general formula (1):

$$M(BH_4)  \quad (1)$$

wherein M represents one selected from the group consisting of alkali metals, alkaline earth metals, aluminum, zinc, quaternary ammoniums, and amines, and m indicates the number of valence of M, ranging from 1 to 4.

The alkali metals represented by M include Na, K and Li. The alkaline earth metals include Mg and Ca. Examples of quaternary ammoniums and amines are tetramethylammonium and tetrabutylammonium.

Borohydrides represented by the general formula (1) include lithium borohydride, sodium borohydride, potassium borohydride, tetramethylammonium borohydride, calcium borohydride, and zinc borohydride, a preference being given to sodium borohydride.

The inorganic reducing agent is used in the forms of original powder, aqueous solution, or alkaline aqueous solution, and it can also be dissolved or uniformly dispersed in the monoalkanol amine or in an alkali catalyst used in the second step.

The amount of the inorganic reducing agent is not particularly limited, and it is preferably 0.001 to 5.0% by weight, more preferably 0.01 to 1.0% by weight of the starting fatty acid. The inorganic reducing agent may be added at any time after the completion of the first step reaction. For example, it may be added at the same time with the charging for the second step when an alkali catalyst is added to the system or after the completion of the transformation of amido ester to monoalkanol amine catalyzed by an alkali catalyst.

Other conditions including the reaction temperature, and reaction duration are not particularly limited, and the same conditions as those in Embodiment 1 may be used.

The hue of the monoalkanol amide obtained by the present invention may be evaluated by the measurement with a colorimeter. The hue of the monoalkanol amide obtained is judged to be "good" when it gives a Gardner score of 1 or 2.

EXAMPLES

The present invention is hereinafter described in more details by means of the following working examples, comparative examples and reference examples but the present invention is not limited by them in any manner.

Example 1

Three-hundred grams, 1.5 mole, of lauric acid was placed in a 500-ml four-necked flask and heated to 160° C. Next, 73.3 g, 1.2 mole, of monoethanolamine (76% by weight of the entire amount) was added to the flask and allowed to react for 3 hours. Thereafter, the pressure of the reaction system was reduced to 30 mm Hg, and the reaction was continued further for 7 hours. Then the mixture was cooled to 90° C., to which 22.9 g (0.38 mole) of monoethanolamine and 8.1 g (0.036 mole) of 24% by weight sodium methylate methanol solution were added under Atmospheric pressure. After the pressure was reduced to 50 mm Hg, the reaction mixture was allowed to react for 30 minutes. Principal reaction conditions and results are listed in Tables 1 and 2.

In the present and subsequent Examples, reaction products in each reaction step were analyzed using gas chromatography and the reaction percentage (mole %) for each reaction product, expressed as the molar percentage of the fatty acid converted to the reaction product, was obtained.

Example 2

Five-hundred kilograms, 2.5 kmole, of lauric acid was placed in a 1.0 m³ reaction vessel and heated to 150° C. Next, 122.2 kg, 2.0 kmole, of monoethanolamine (77% by weight of the entire amount) was added to the vessel and allowed to react for 3 hours. Thereafter, the pressure of the reaction system was reduced to 30 mm Hg, and the reaction was continued further for 7 hours. Then, the mixture was cooled to 90° C., to which 36.7 kg (0.6 kmole) of monoethanolamine was added under atmospheric pressure and allowed to react for 30 minutes. To the reaction mixture, 8.4 kg (37.5 mole) of 24% by weight sodium methylate methanol solution was added, followed by pressure reduction to 30 mm Hg. The mixture was subjected to a methanol topping treatment for 30 minutes. Here, the "methanol topping treatment" is to distill away the methanol solvent used when sodium methylate, a catalyst, was added.

Principal reaction conditions and results are listed in Tables 1 and 2.

Example 3

Three-hundred grams, 1.5 mole, of lauric acid was placed in a 500-ml four-necked flask and heated to 160° C. Next, 82.5 g, 1.35 mole, of monoethanolamine (82% by weight of the entire amount) was added to the flask and allowed to react for 10 hours in a nitrogen gas stream under atmospheric pressure. Next, the reaction mixture was cooled to 90° C., to which 18.3 g (0.3 mole) of monoethanolamine and 6.75 g (0.03 mole) of 24% by weight sodium methylate methanol solution were added under atmospheric pressure. After the pressure was reduced to 50 mm Hg, the reaction mixture was allowed to react for 1 hour. Principal reaction conditions and results are listed in Tables 1 and 2.

Example 4

Three-hundred grams, 1.5 mole, of lauric acid was placed in a 500-ml four-necked flask and heated to 160° C. Next, 73.0 g, 1.2 mole, of monoethanolamine (79% by weight of the entire amount) was added to the flask and allowed to react for 5 hours. Thereafter, the pressure of the reaction system was reduced to 50 mm Hg, and the reaction was continued further for 7 hours. Then the mixture was cooled to 90° C., to which 19.4 g (0.32 mole) of monoethanolamine and 5.8 g (0.026 mole) of 24% by weight sodium methylate methanol solution were added under atmospheric pressure. The reaction mixture was allowed to react for 30 minutes. Thereafter, the pressure was reduced to 10 mm Hg, and the reaction mixture was subjected to methanol topping for one hour. Principal reaction conditions and results are listed in Tables 1 and 2.

Example 5

In a 5-L four-necked flask, 3000 g, 15.0 mole, of lauric acid was placed and heated to 160° C. Next, 732.1 g, 12.0 mole, of monoethanolamine (79% by weight of the entire amount) was added to the flask and allowed to react for 5 hours. Thereafter, the pressure of the reaction system was reduced to 50 mm Hg, and the reaction was continued further for 7 hours. Next, the mixture was cooled to 90° C., to which 192.2 g (3.1 mole) of monoethanolamine and 125.0 g (0.56 mole) of 24% by weight sodium methylate methanol solution were added under atmospheric pressure. The reaction mixture was allowed to react for 30 minutes. Thereafter, the pressure was reduced to 10 mm Hg, and the reaction mixture was subjected to methanol topping treatment for one hour. Principal reaction conditions and results are listed in Tables 1 and 2.

Example 6

In a 5-L four-necked flask, 3000 g, 15.0 mole, of lauric acid was placed and heated to 160° C. Next, 732.1 g, 12.0 mole, of monoethanolamine (79% by weight of the entire amount) was added to the flask and allowed to react for 5 hours. Thereafter, the pressure of the reaction system was reduced to 50 mm Hg, and the reaction was continued further for 7 hours. Next, the mixture was cooled to 90° C., to which 192.2 g (3.1 mole) of monoethanolamine and 168.8 g (0.75 mole) of 24% by weight sodium methylate methanol solution were added under atmospheric pressure. The reaction mixture was allowed to react for 30 minutes. Thereafter, the pressure was reduced to 10 mm Hg, and the reaction mixture was subjected to a methanol topping treatment for one hour. Principal reaction conditions and results are listed in Tables 1 and 2.

Comparative Example 1

Three-hundred grams, 1.5 mole, of lauric acid was placed in a 500-ml four-necked flask and heated to 150° C. Next, 110 g, 1.8 mole, of monoethanolamine was added to the flask and allowed to react for 8 hours. The results are shown in Table 2.

Comparative Example 2

Monoalkanol amides were produced according to the method described in JP-B-56-49903. Three-hundred grams, 1.5 mole, of lauric acid was placed in a 500-ml four-necked flask and heated to 150° C. Next, 55.0 g, 0.9 mole, of monoethanolamine (55% by weight of the entire amount) was added to the flask and allowed to react for 10 hours in a nitrogen gas stream. Next, the reaction mixture was cooled to 90° C., to which 45.8 g (0.75 mole) of monoethanolamine in which 2.7 g of sodium hydroxide (0.0675 mole) had been dissolved was added under atmospheric pressure. The reaction mixture was allowed to react for 4 hours. The results are listed in Table 2.

Reference Example 1

Figure 2:
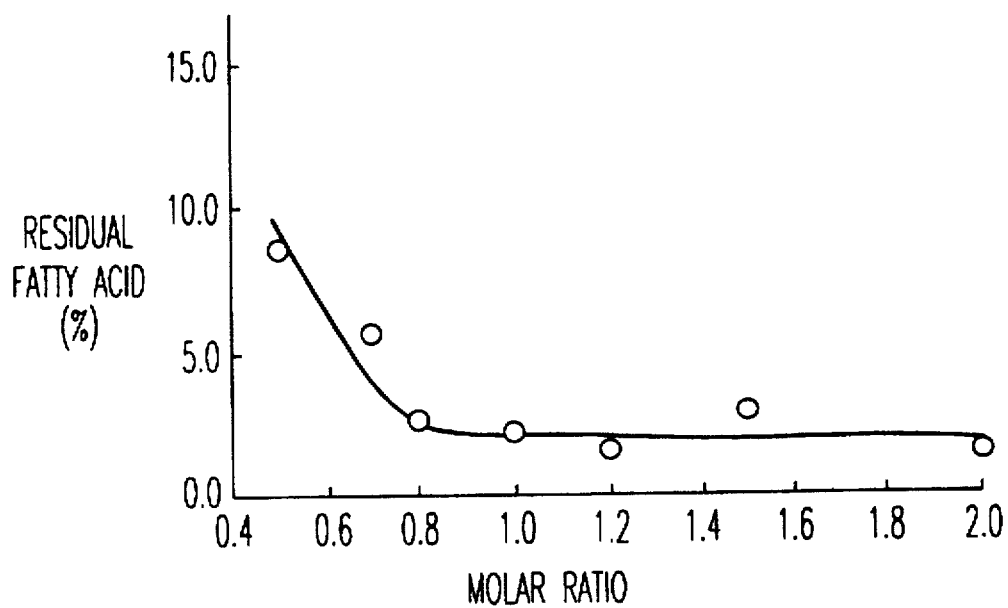
FIG. 2 is a graph which shows the effect of the molar ratio of monoalkanol amine to fatty acid on the amount of residual or unreacted fatty acid.

The molar ratio of monoalkanol amine to fatty acid was studied for its effects on the reaction selectivity toward amino ester formation and on the amount of residual fatty acid. Lauric acid is used as a fatty acid, and monoethanolamine, as a monoalkanol amine. Lauric acid and monoethanolamine were mixed at varying molar ratios (lauric acid: monoethanol amine) of 0.5, 0.7, 0.8, 1.0, 1.2, 1.5, and 2.0. Each mixture was allowed to react at 160° C. for 8 hours under atmospheric pressure. The resulting mixtures were analyzed for the reaction products in the same manner as in Example 1. The results are shown in FIGS. 1 and 2. The reaction selectivity toward amino ester formation is expressed as the molar percentage (mole%) of the fatty acid converted to amino ester.

TABLE 1

|  | Example 1 | Example 2 | Example 3 | Example 4 | Example 5 | Example 6 |
| --- | --- | --- | --- | --- | --- | --- |
| Molar ratio* (Entire amount) First step reaction | 1.05 | 1.04 | 1.1 | 1.01 | 1.01 | 1.01 |
| Monoethanolamine (% by wt.) | 76 | 77 | 82 | 79 | 79 | 79 |

TABLE 1-continued

|  | Example 1 | Example 2 | Example 3 | Example 4 | Example 5 | Example 6 |
|---|---|---|---|---|---|---|
| Temperature (°C.) | 160 | 150 | 160 | 160 | 160 | 160 |
| Pressure |  |  |  |  |  |  |
| ① Pressure · duration | Atm.** · 3 hr | Atm.** · 3 hr | Atm.** · 10 hr | Atm.** · 5 hr | Atm.** · 5 hr | Atm.** · 5 hr |
| ② Pressure · duration | 30 mmHg/7 hr | 30 mmHg/7 hr | — | 50 mmHg/7 hr | 50 mmHg/7 hr | 50 mmHg/7 hr |
| Second step reaction |  |  |  |  |  |  |
| Monoethanolamine (% by wt.) | 24 | 23 | 18 | 21 | 21 | 21 |
| Temperature (°C.) | 90 | 90 | 90 | 90 | 90 | 90 |
| Pressure (mmHg) | 50 | 30 | 50~Atm.** | 10~Atm.** | 10~Atm.** | 10~Atm.** |
| Catalyst*** | 2.4 | 1.5 | 2.0 | 1.7 | 3.7 | 5.0 |

*Monoethanolamine/fatty acid
**Atmospheric pressure
***Expressed as mol % of the amount of the starting fatty acids

TABLE 2

|  | Example 1 | Example 2 | Example 3 | Example 4 | Example 5 | Comparative Example 1 | Comparative Example 2 | Example 6 |
|---|---|---|---|---|---|---|---|---|
| First step reaction |  |  |  |  |  |  |  |  |
| Monoethnolamide | 47.1 | 59.0 | 69.3 | 48.1 | 49.0 | — | 12.0 | 49.0 |
| Amino monoester | 0.1 | 0.1 | 0.7 | 0.1 | 0.1 | — | 0.4 | 0.1 |
| Amido monoester | 51.5 | 39.8 | 29.0 | 50.8 | 49.9 | — | 85.4 | 49.9 |
| Residual fatty acid | 1.3 | 1.1 | 1.0 | 1.0 | 1.0 | — | 2.2 | 1.0 |
| Second step reaction |  |  |  |  |  |  |  |  |
| Monoethanolamide | 98.0 | 98.1 | 97.9 | 98.5 | 98.6 | 93.0 | 95.7 | 98.8 |
| Amino monoester | 0.3 | 0.4 | 0.9 | 0.3 | 0.2 | 4.7 | 0.4 | 0.2 |
| Amido monoester | 0.4 | 0.4 | 0.2 | 0.2 | 0.2 | 0.9 | 1.7 | 0.0 |
| Residual fatty acid | 1.3 | 1.1 | 1.0 | 1.0 | 1.0 | 1.4 | 2.2 | 1.0 |

Note: Values are molar percentages (mol %) the fatty acid converted to the corresponding reaction products.

The following facts were found from the results of the above analysis.

The production method of the present invention provided highly pure monoethanolamide with low contents of residual fatty acid and by-products (Examples 1 to 6).

When the reaction was carried out in one step (Comparative Example 1), the purity of the resulting monoethanolamide was lower than that obtained by the present invention, the obtained monoethanolamide containing high amounts of residual fatty acid and byproducts. When the amount of monoethanolamine used in the first step reaction was not more than 70% by weight of the entire amount (Comparative Example 2), the purity of the resulting monoethanolamide was lower than that obtained by the present invention and the amount of the alkali catalyst required was higher than that in the present invention.

Also, from FIG. 1, it was found that the reaction selectivity toward amino ester formation is maximized when the molar ratio of monoalkanol amine to fatty acid is around 1. From FIG. 2, it was found that the amount of residual fatty acid was sharply increased when the molar ratio of monoalkanol amine to fatty acid is not more than 0.7.

Example 7

In a 500-ml four-necked flask, 200.4 g, 1.0 mole, of lauric acid was placed and heated to 160° C. Next, 48.9 g, 0.8 mole, of monoethanolamine (73% by weight of the entire amount) was added to the flask and allowed to react for 5 hours in a nitrogen gas stream under atmospheric pressure. Thereafter, the pressure of the reaction system was reduced to 50 mm Hg, and the reaction was continued further for 7 hours. Then the mixture was cooled to 90° C., to which 18.3 g (0.3 mole) of monoethanolamine containing 0.2 g of sodium borohydride uniformly dispersed therein and 7.16 g (0.04 mole) of 28% by weight sodium methylate methanol solution were added under atmospheric pressure. The reaction mixture was allowed to react for 30 minutes. After the pressure was reduced to 10 mm Hg, the reaction mixture was allowed to react further for 1 hour.

The hue of the reaction product was measured using color comparison tubes. The product was evaluated as Gardner 1.

Example 8

The first step reaction was carried out in the same manner as in Example 7. After the reaction was continued for 7 hours, the reaction mixture was cooled to 90° C., to which monoethanolamine and sodium methylate was added in the same manner as in Example 7 under atmospheric pressure. The reaction mixture was allowed to react for 30 minutes. After the pressure was reduced to 10 mm Hg, the reaction mixture was allowed to react for further 1 hour. Thereafter, 0.2 g of sodium borohydride powder was added, and the reaction mixture was allowed to react for further 30 minutes at 90° C.

The hue of the reaction product was measured using color comparison tubes. The product was evaluated as Gardner 2.

Reference Example 2

The same procedures as in Example 7 were followed except that sodium borohydride was dispersed in the monoethanolamine used in the first step reaction and added to the reaction system.

The hue of the reaction product was measured using color comparison tubes. The product was evaluated as Gardner 3.

Reference Example 3

The same procedures as in Example 7 were followed except that sodium borohydride was not used. The hue of the reaction product was measured using color comparison tubes. The product was evaluated as Gardner 4.

From the results of the above Examples and Reference Examples, it was found that monoethanolamide with good hue can be obtained by adding an inorganic reducing agent in the second step reaction.

Reference Example 4

The effects of the following factors upon the resulting monoalkanol amide were examined: the molar ratio of the entire amount of monoalkanol amine used for the entire reaction to the amount of fatty acid; the molar ratio of the amount of monoalkanol amine used in the first step reaction to the amount of fatty acid; and % by weight of the amount of monoalkanol amine used in the first step reaction of the entire amount of monoalkanol amine used in the entire reaction. Lauric acid was used as the fatty acid, and monoethanolamine, as the monoalkanol amine. The similar procedures as those in Example 1 were followed. The reaction conditions and the results are shown in Table 3.

mine added in the second step reaction was higher for sample No. 10 than those for sample Nos. 4 and 7 for which the same reaction conditions were employed in the first step reaction, the purity of monoethanolamide in the final reaction products was low.

Example 9

To the lauric acid monoethanolamide, 243 g, synthesized in Example 6, 132 g of ethyleneoxide was introduced at 90° to 100° C. under gauge pressure of 0 to 4 atm. over 1.5 hours. The resulting polyoxyethylene lauric acid amide, 375 g, was subjected to pressure reduction to 50 mm Hg, with keeping the temperature at 70° to 75° C., to which 291 g of 40% by weight sodium monochloroacetate aqueous solution and 88 g of 48% by weight sodium hydroxide aqueous solution were added over 5 hours with continuing dehydration under the conditions that the pH in the reaction system was maintained at 8 to 12, and the temperature and the degree of pressure reduction was kept unchanged. With further keeping the temperature and the degree of pressure reduction unchanged, the mixture was allowed to react for 1 hour. After the pressure was increased to atmospheric pressure, 10 g of water was added to the reaction mixture, which was then allowed to react at 85° C. for further 1 hour

TABLE 3

| Sample No. | 1 | 2 | 3 | 4 | 5 | 6 | 7 | 8 | 9 | 10 |
|---|---|---|---|---|---|---|---|---|---|---|
| Molar ratio* (Entire amount) | 0.9 | 1.0 | 1.0 | 1.0 | 1.0 | 1.0 | 1.1 | 1.1 | 1.2 | 1.3 |
| Amount of monoethanol amine added in the first step reaction | | | | | | | | | | |
| Molar ratio** | 0.80 | 0.60 | 0.71 | 0.80 | 0.90 | 1.00 | 0.80 | 0.90 | 0.90 | 0.80 |
| % by weight*** | 88.8 | 60.0 | 71.0 | 80.0 | 90.0 | 100 | 72.7 | 81.8 | 75.0 | 61.5 |
| Products in the second step reaction**** | | | | | | | | | | |
| Monoethanolamide | 88.0 | 96.1 | 97.9 | 98.6 | 97.9 | 91.7 | 98.6 | 98.0 | 97.9 | 98.6 |
| Amino monoester | 0.4 | 0.3 | 0.3 | 0.2 | 0.9 | 7.0 | 0.2 | 0.8 | 0.9 | 0.3 |
| Amido monoester | 0.6 | 1.0 | 0.3 | 0.2 | 0.2 | 0.2 | 0.2 | 0.2 | 0.2 | 0.1 |
| Residual fatty acid | 11.0 | 2.6 | 1.5 | 1.0 | 1.0 | 1.1 | 1.0 | 1.0 | 1.0 | 1.0 |

*Monoethanolamine/fatty acid
**To the molar amount of fatty acid
***Weight % of the entire amount of monoethanolamine
****Mol % of the fatty acid converted to the corresponding reaction products.

The results as shown above indicate that the purity of the monoethanolamide obtained by the method of the present invention is high, with small contents of residual fatty acid and by-products (Sample Nos. 3–5 and 7–9).

As for sample No. 1, the molar ratio of the entire amount of monoethanolamine to the amount of fatty acid was below the range of the present invention, resulting in the monoethanolamide with a high residual fatty acid content. As for sample No. 2, the amount of monoethanolamine added in the first step reaction was below the range of the present invention, resulting in monoethanolamide of low purity containing a large amount of residual fatty acid. As for sample No. 6, the amount of monoethanolamine added in the first step reaction was too large, resulting in monoethanolamide of low purity containing a high amount of amino ester. As for sample No. 10, although the purity of the resulting monoethanolamide, as expressed by mole % of the fatty acid converted to the monoethanolamide, was high, the final product of this sample was subject to coloration during storage. Because the amount of the residual monoethanolato yield the product mainly containing the compound represented by the following formula:

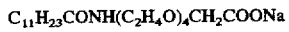

$C_{11}H_{23}CONH(C_2H_4O)_4CH_2COONa$

Comparative Example 3

The same procedures as in Example 9 were carried out except that lauric acid monoethanolamide synthesized in Comparative Example 1 was used instead of lauric acid monoethanolamide synthesized in Example 6.

With the products obtained in the above Examples and Comparative Examples, a foaming test and a storage stability test were performed. The results of these tests are shown in Table 4. The forming test was carried out as follows: a 5% by weight aqueous solution of each sample was prepared, and 100 ml of this solution (Temperature of the solution: 40° C.) was injected into a graduated cylinder. A stirring impeller was placed in the solution. After 30-second stirring, the volume (mL) of the foaming was measured. The forming volume was evaluated according to the following criteria:

O (good): not less than 200 mL

Δ (fair): not less than 180 mL and less than 200 mL x (poor): less than 180 mL

The storage stability test was carried out as follows: a 20% by weight aqueous solution of the dried solid of each sample was stored at −5° C. for 20 days. The storage stability of each sample was evaluated in terms of turbidity:

O (good): clear x (Poor): turbid

TABLE 4

|  | Foam volume | Storage stability |
|---|---|---|
| Example 9 | o | o |
| Comparative Example 3 | x | x |

Obviously, numerous modifications and variations of the present invention are possible in light of the above teachings. It is therefore to be understood that within the scope of the appended claims, the invention may be practiced otherwise than as specifically described herein.

This application is based upon Japanese Applications 7-225911 and 7-354491, filed in the Japanese Patent Office on Aug. 9, 1995 and Dec. 28, 1995, respectively, the entire contents of which are hereby incorporated by reference.

What is claimed as new and desired to be secured by Letters Patent of the United States is:

1. A method for producing a monoalkanol amide comprising the steps of:
   (a) reacting a fatty acid with a first amount of a monoalkanol amine to yield a mixture comprising a monoalkanol amide and an amido monoester, said first amount of said monoalkanol amine being a molar amount of from 0.7 to 0.95 times a molar amount of said fatty acid; and
   (b) reacting said mixture obtained in (a) with a second amount of said monoalkanol amine; wherein,
   said first amount of monoalkanol amine is between 70–90% by weight of said first amount and said second amount of monoalkanol amine combined; and
   wherein a molar ratio of said first amount and said second amount of monoalkanol amine combined to said fatty acid is 1.0 to 1.3.

2. The method according to claim 1, wherein step (b) reaction is carried out in the presence of an alkali catalyst.

3. The method according to claim 2, wherein step (b) is carried out in the presence of an inorganic reducing agent.

4. The method according to claim 3, wherein said inorganic reducing agent is selected from the group consisting of hydrogen, sodium sulfite, potassium sulfite, sodium thiosulfate, potassium thiosulfate, borohydride salts, aluminum hydride salts, and a mixture thereof.

5. The method according to claim 4, wherein said borohydride salts are represented by the following formula (1):

wherein M is selected from the group consisting of alkali metals, alkaline earth metals, aluminum, zinc, quaternary ammoniums, and amines, and m indicates the number of valence of M, ranging from 1 to 4.

6. The method according to claim 3, wherein said inorganic reducing agent is an amount of 0.001 to 5.0% by weight of said fatty acid.

7. The method according to claim 1, wherein said fatty acid is represented by the following general formula (2):

wherein $R^1$ represents a linear or branched alkyl, alkenyl or hydroxyalkyl group, each having 7 to 23 carbon atoms.

8. The method according to claim 1, wherein said monoalkanol amine is a compound represented by the following general formula (3):

$$R^2\text{—}NH_2 \qquad (3)$$

wherein $R^2$ represents a linear alkanol group having 1 to 4 carbon atoms or a branched alkanol group having 3 or 4 carbon atoms.

9. The method according to claim 1, wherein step (a) is carried out at a temperature of from 100° to 170° C. and wherein step (b) is carried out at a temperature of from 85° to 110° C.

10. The method according to claim 1, wherein step (a) is carried out under a pressure of from 3 mm Hg to atmospheric pressure.

11. The method according to claim 8, wherein said monoalkanol amine is selected from the group consisting of monomethanolamine, monoethanolamine, monoisopropanolamine, and a mixture thereof.

12. The method according to claim 11, wherein said monoalkanol amine is monoethanolamine.

13. The method according to claim 2, wherein said alkali catalyst is a metal alkoxide.

14. The method according to claim 13, wherein said metal alkoxide is selected from the group consisting of sodium methylate, sodium ethylate, potassium methylate, potassium ethylate, and a mixture thereof.

15. The method according to claim 7, wherein said fatty acid is selected from the group consisting of capric acid, caprylic acid, undecanoic acid, lauric acid, myristic acid, pentadecanoic acid, palmitic acid, stearic acid, oleic acid, arachidic acid, behenic acid, and a mixture thereof.

16. The method according to claim 7, wherein said fatty acid is derived from a compound selected from the group consisting of coconut oil, beef tallow, palm oil, palm kernel oil, and a mixture thereof.

17. The method according to claim 7, wherein said fatty acid is a synthetic fatty acid produced by paraffin oxidation or by the oxo process.

18. A composition, comprising a monoalkanol amide produced by a process comprising the steps of:
   (a) reacting a fatty acid with a first amount of a monoalkanol amine to yield a mixture mainly comprising a monoalkanol amide and an amido monoester, said first amount of said monoalkanol amine being a molar amount of from 0.7 to 0.95 times a molar amount of said fatty acid; and
   (b) reacting the mixture obtained in (a) with a second amount of said monoalkanol amine; wherein,
   said first amount is between 70–90% by weight of said first amount and said second amount combined; and
   wherein a molar ratio of said first amount and said second amount combined to said fatty acid is 1.0 to 1.3.

19. A composition, comprising a monoalkanol amide having a Gardner score of 1 to 2.

* * * * *